US006768121B2

(12) United States Patent
Horsky et al.

(10) Patent No.: US 6,768,121 B2
(45) Date of Patent: Jul. 27, 2004

(54) ION SOURCE HAVING REPLACEABLE AND SPUTTERABLE SOLID SOURCE MATERIAL

(75) Inventors: Thomas N. Horsky, Boxborough, MA (US); Tommy D. Hollingsworth, Leander, TX (US)

(73) Assignee: Axcelis Technologies, Inc., Beverly, MA (US)

( * ) Notice: Subject to any disclaimer, the term of this patent is extended or adjusted under 35 U.S.C. 154(b) by 0 days.

(21) Appl. No.: 10/386,262

(22) Filed: Mar. 11, 2003

(65) Prior Publication Data

US 2004/0000651 A1 Jan. 1, 2004

Related U.S. Application Data

(63) Continuation of application No. 09/633,322, filed on Aug. 7, 2000, now Pat. No. 6,583,544.

(51) Int. Cl.[7] ............................ A61N 5/00; G21G 5/00
(52) U.S. Cl. ................. 250/427; 313/359.1; 250/492.2; 250/492.3
(58) Field of Search ........................ 250/427; 313/359.1

(56) References Cited

U.S. PATENT DOCUMENTS

| | | | | |
|---|---|---|---|---|
| 4,016,421 A | | 4/1977 | Hull et al. | |
| 4,166,952 A | | 9/1979 | Colby et al. | |
| 5,216,330 A | | 6/1993 | Ahonen | |
| 5,497,006 A | | 3/1996 | Sferlazzo et al. | |
| 5,523,652 A | | 6/1996 | Sferlazzo et al. | |
| 5,703,372 A | | 12/1997 | Horsky et al. | |
| 5,852,345 A | | 12/1998 | Armini | |
| 5,886,355 A | | 3/1999 | Bright et al. | |
| 5,904,778 A | | 5/1999 | Lu et al. | |
| 6,084,241 A | * | 7/2000 | Sitter | 250/492.21 |
| 6,227,140 B1 | | 5/2001 | Kennedy et al. | |
| 6,583,544 B1 | * | 6/2003 | Horsky et al. | 313/359.1 |

FOREIGN PATENT DOCUMENTS

| | | |
|---|---|---|
| JP | 10-188833 A | 7/1998 |

* cited by examiner

*Primary Examiner*—John R. Lee
*Assistant Examiner*—James J. Leybourne
(74) *Attorney, Agent, or Firm*—Eschweiler & Associates, LLC

(57) ABSTRACT

An ion source (10) for an ion implanter is provided, comprising: (i) an ionization chamber (14) defined at least partially by chamber walls (12), and having an inlet (45) into which a sputtering gas may be injected and an aperture (18) through which an ion beam (B) may be extracted: (ii) an ionizing electron source (44) for ionizing the sputtering gas to form a sputtering plasma; and (iii) a sputterable repeller (100). The sputterable repeller both (a) repels electrons emitted by the electron source, and (b) provides a source of sputtered material that can be ionized by the electron source. the sputterable repeller (100) comprises a slug (108) of sputterable material, and further comprises mounting structure (102, 104) for removably mounting the slug within the ionization chamber (14), so that the slug is made removably detachable from the mounting structure. The sputterable material may be any of the following elements, or compounds including any of these elements: aluminum (Al), boron (B), beryllium (Be), carbon (C), cesium (Cs), germanium, (Ge), molybdenum, (Mo), antimony (Sb), or silicon (Si). The repeller (100) is negatively biased with respect to the ionization chamber walls (12), and may be continuously variably biased to provide for a wide dynamic range of resulting ion beam currents.

9 Claims, 3 Drawing Sheets

ION SOURCE HAVING REPLACEABLE AND SPUTTERABLE SOLID SOURCE MATERIAL

RELATED APPLICATIONS

This application is a continuation of Ser. No. 09/633,322 filed Aug. 7, 2000 now U.S. Pat. No. 6,583,544, which is entitled "Ion Source Having Replaceable and Sputterable Solid Source Material".

The following U.S. patent application is incorporated by reference herein as if it has been fully set forth: application Ser. No. 09/633,324, filed on Aug. 7, 2000, entitled "Magnet for Generating a Magnetic Field in an Ion Source", and having a filing date coincident with the present application.

FIELD OF THE INVENTION

The present invention relates generally to the field of semiconductor processing systems such as ion implanters, and more specifically to an ion source for use in such an ion implanter, having a replaceable and sputterable solid source material contained therein.

BACKGROUND OF THE INVENTION

In the large-scale manufacture of integrated circuits, ion implantation has become a standard accepted technology of industry to dope workpieces such as silicon wafers with impurities. Conventional ion implantation systems include an ion source that ionizes a desired dopant element which is then accelerated to form an ion beam of a prescribed energy. The ion beam is directed at the surface of the workpiece to implant the workpiece with the dopant element. The energetic ions of the ion beam penetrate the surface of the workpiece so that they are embedded into the crystalline lattice of the workpiece material to form a region of desired conductivity. The implantation process is typically performed in a high vacuum process chamber which prevents dispersion of the ion beam by collisions with residual gas molecules and which minimizes the risk of contamination of the workpiece by airborne particulates.

Ion dose and energy are the two most important variables used to define an implant step. Ion dose relates to the concentration of implanted ions for a given semiconductor material. Typically, high current implanters (generally capable of generating tens of milliamps (mA) of ion beam current are used for high dose implants while medium current implanters (generally capable up to about 1 mA beam current) are used for lower dose applications. Ion energy is used to control junction depth in semiconductor devices. The energy levels of the ions that comprise the ion beam determine the degree of depth of the implanted ions. High energy processes such as those used to form retrograde wells in most semiconductor devices require implants of up to a few million electron volts (MeV), while shallow junctions may only demand energies below 1 thousand electron voles (keV).

Conventional ion sources utilize an ionizable dopant gas that is obtained either directly from a source of a compressed gas or indirectly from a solid from which has been vaporized. Typical source elements are boron (B), phosphorous (P), gallium (Ga), indium (In), antimony (Sb), and arsenic (As). These source elements can be provided in solid form or in gaseous form, such as boron, which may be provided in either solid form (B) or in gaseous form as boron trifluoride ($BF_3$). $BF_3$, however, suffers from the disadvantages of being toxic and flammable, as well as being corrosive to implanter surfaces due to its fluorine component.

A typical ion source 10 for obtaining atoms for ionization from a solid or gaseous form is shown in FIG. 1. This type of ion source comprises an arc chamber AC, which functions as an anode, and a filament F contained therein which functions as a cathode. In operation, an arc voltage is applied between the filament F and the walls of the arc chamber AC. The energized filament thermionically emits high-energy electrons E that are accelerated toward the electrically grounded (i.e., relatively positively based) chamber wall. A gas containing boron or phosphorous is fed into the arc chamber AC via an inlet I.

A repeller R is positioned within the arc chamber AC opposite the filament F. The repeller electrostatically repels the filament-emitted electrons E to confine these electrons to a path P1 within an ionization region between the filament and the repeller. The electrons E collide with and dissociate and/or ionize the gas molecules in the ionization region, where the number of collisions with ionizable gas molecules is maximized. Positive ions are created when an electron is removed from the outer shell of these gas molecules by the filament-emitted electrons E. In this manner, a plasma is created comprised at least partially of positively charged ions. A generally positively charged ion beam is drawn from this plasma, typically through a source aperture SA in the arc chamber, by means of an electrode at negative bias (not shown).

A source magnet SM increases ionization efficiency in the arc chamber by setting up a magnetic field along the chamber. The magnetic field causes the path P1 of the electrons E traveling through the arc chamber to be helical, which further increases the yield of collisions with the gas molecules, thereby creating more useful ions. The source magnet current is adjusted to maximize the extracted ion beam current and ion beam quality.

The repeller R is typically made of metal, for example, molybdenum (Mo). The repeller is permitted to reside at a floating electrical potential. A ceramic insulator C insulates both the filament and the repeller from the walls of the arc chamber, which are typically maintained at ground potential. The filament F and the repeller R are thereby electrically and thermally isolated from each other and from the arc chamber walls.

When ions need to be obtained from a solid source, the walls of the arc chamber may be constructed of or lined with a sputterable source material such as boron, as in Japanese Patent Application No. 96JP-356494, filed Dec. 26, 1996 (Publication No. 10-188833, published Jul. 21, 1998). In such a sputter ion source, an inert carrier gas such a argon (Ar) is fed into the arc chamber AC via inlet I and is ionized by the filament F to create an ionized plasma. The ionized plasma then sputter etches material from the boron liner, which in turn is dissociated and/or ionized by the electrons emitted from filament F. The resulting positive boron ions and positive argon ions are extracted through the source aperture SA in the form of an ion beam. The ion beam is subsequently mass analyzed to remove the argon ions to produce an ion beam comprised substantially of ionized boron atoms.

Known sputter ion sources, however, require the sputterable wall liners to be replaced after they have been sufficiently eroded by the sputtering process. In addition, the repeller must be maintained, as it may become eroded over time. Still further, if the sputterable wall liners are changed to effect a different ion species (i.e., from boron (B) to phosphorous (P), previously sputtered material coated on the repeller may pose a risk of ion species contamination. Thus, to effect an ion beam species change, both the sputterable wall liners and the repeller must be changed.

Accordingly, it is an object of the present invention to provide a mechanism for including a sputterable solid source material for an ion implanter ion source, while minimizing the maintenance required to effect a change of source materials. It is a further object of the invention to provide a repeller for an ion implanter ion source that functions both as a repeller and as a sputterable solid source material. It is yet a further object of the invention to provide a mechanism for controlling the characteristics of the ion beam by actively controlling the voltage applied to the repeller.

SUMMARY OF THE INVENTION

An ion source for an ion implanter is provided, comprising: (i) an ionization chamber defined by chamber walls, and having an inlet into which a sputtering gas may be injected and an aperture through which an ion beam may be extracted; (ii) an ionizing electron source for ionizing the sputtering gas to form a sputtering plasma; and (iii) a sputterable repeller disposed within the chamber. The sputterable repeller both (i) repels electrons emitted by the electron source, and (ii) provides a source of sputtered material that can be ionized by the electron source. The sputterable repeller comprises a slug of sputterable material, and further comprises mounting structure for mounting the slug within the ionization chamber, so that the slug is made removably detachable from the mounting structure.

The sputterable material may be any of the following elements, or a compound including any of these elements: aluminum (Al), boron (B), beryllium (Be), carbon (C), cesium (Cs), germanium, (Ge), molybdenum, (Mo), antimony (Sb), or silicon (Si). The repeller is negatively biased with respect to the ionization chamber walls, and may be continuously variably biased to provide for a wide dynamic range of resulting ion beam currents.

DETAILED DESCRIPTION OF A PREFERRED EMBODIMENT

Figure 2:
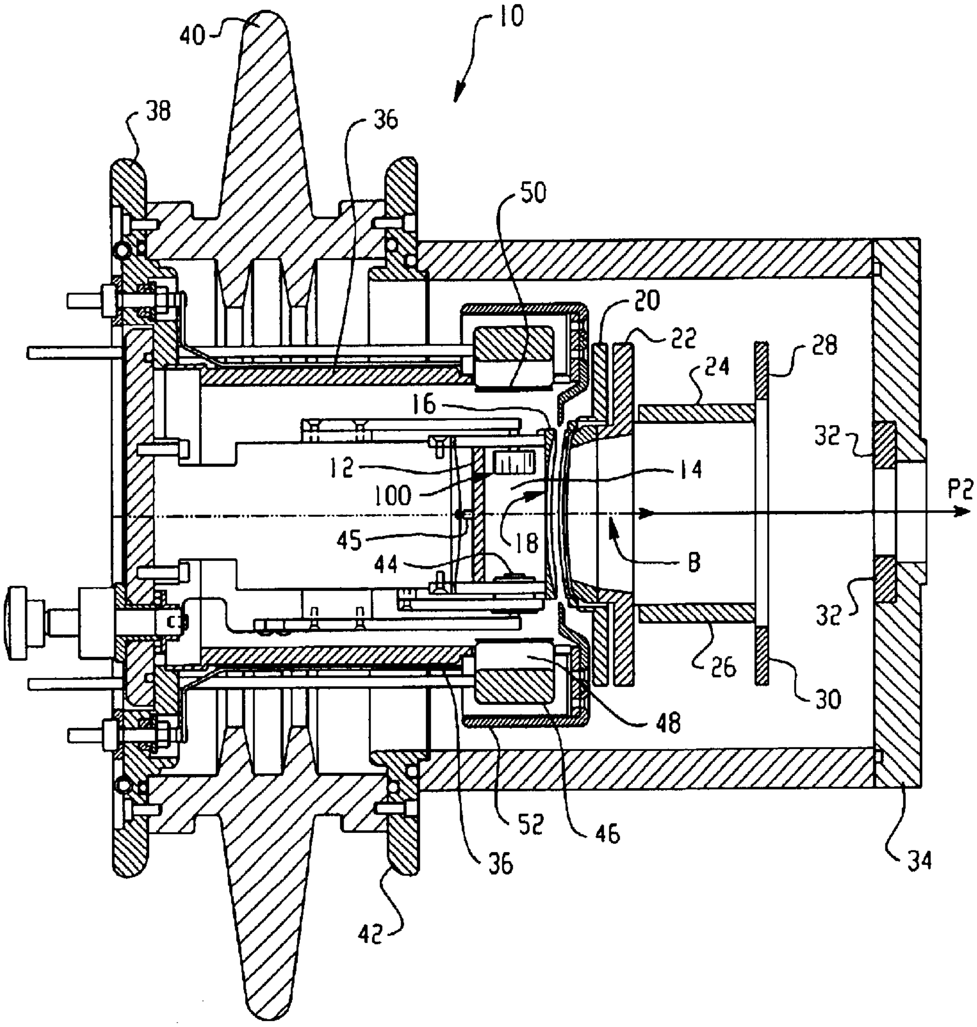
FIG. 2 is a sectional view of an ion source constructed according to the principles of the present invention.

Referring now to the drawings, FIG. 2 shows an ion source 10 for an ion implanter into which is incorporated the inventive repeller 100 of the present invention. The ion source 10 comprises chamber walls 12 that from an ionization chamber 14 in which a plasma is formed. A source aperture plate 16, having an aperture 18 formed therein, permits the ion beam B to be drawn out of the ionization chamber 14 by extraction electrodes 20 and 22 along the path P2.

The extraction electrodes are typically negatively biased with respect to the aperture plate 16 and the other ion source walls 12, so that the ion beam extracted from the ionization chamber is comprised primarily of positive ions. Aluminum support legs 24 and 26 support half rings 28 and 30, respectively, which guide the ion beam B through graphite inserts 32 in the source housing 34.

An ion source assembly support tube 36 surrounds and supports the ionization chamber and abuts a mounting flange 38. An insulator 40 electrically isolates the mounting flange 38 and a flange 42 on the source housing 34. The insulator 40 isolates the source housing 34 from the energization voltages required to generate ions in and accelerate ions away from the arc chamber 14.

Within the chamber walls 12 of the ionization chamber 14 resides a filament (not shown) at least partially contained within an indirectly heated cathode 44, at one end of the chamber, and the repeller 100, located at the other end, opposite the cathode. A sputtering gas such as argon (Ar) is injected into the ionization chamber 14 via inlet 45 and the filament is energized to thermionically emit electrons. These filament-emitted electrons accelerate toward and contact the indirectly heated cathode 44, which in turn emits electrons into the arc chamber 14. The repeller (or anticathode) 100, which resides at a negative electrical potential, as further explained below, repels the electrons back toward the end-cap cathode 44. The repeller 100 thereby functions to centrally confine these cathode-emitted electrons within the chamber, where they have the greatest number of collisions with and subsequent ionization of the sputtering gas molecules.

Surrounding the ionization chamber is a magnet assembly, mounted to the source assembly support tube 36, comprising (i) an annular yoke 46 about which is wound a pair of coils, (ii) magnetic poles 48 which are diametrically opposed to each other and extend from the yoke 46, and (iii) heat shields 50 attached to each of the magnetic poles 48. A non-magnetic shield 52 surrounds the entire magnet assembly to shield the assembly from backstreaming electrons. The magnetic fields are concentrated within the ionization chamber 14 to enhance plasma ionization rates.

Figure 1:
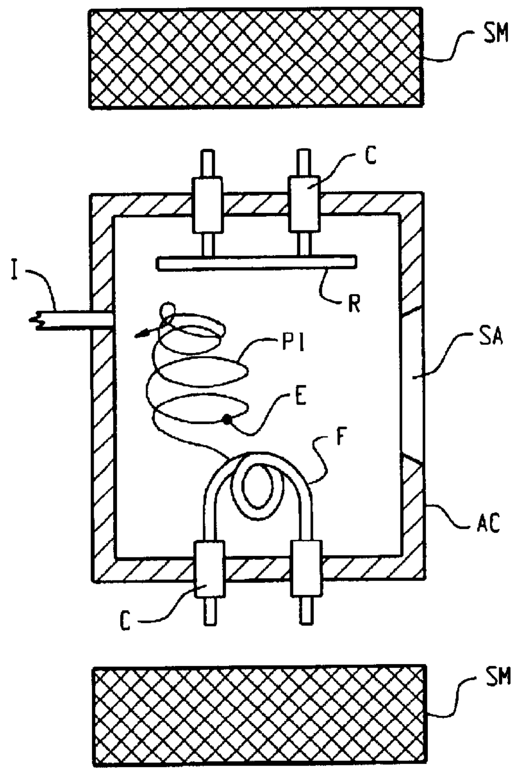
Fig. 1 PRIOR ART
FIG. 1 is a sectional view of a conventional ion source.
Figure 3:
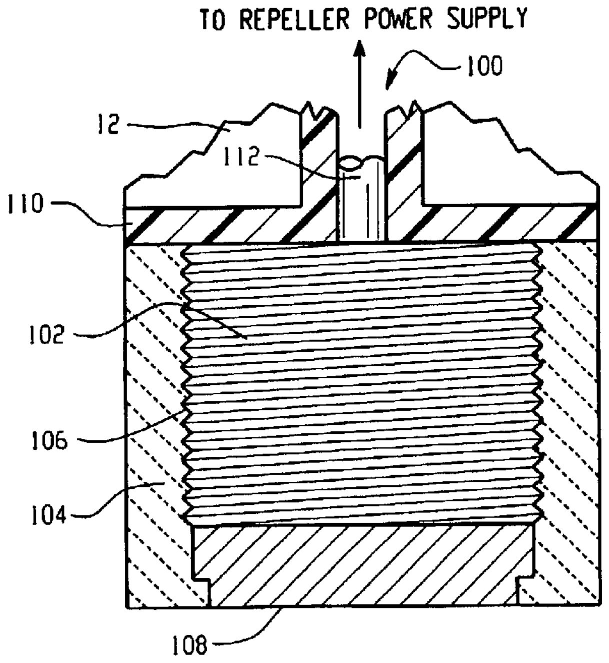
FIG. 3 is a sectional view of the repeller portion of the ion source of FIG. 2.

The ionized sputtering gas generated in the ionization chamber 14 forms a sputtering plasma that impacts the repeller 100, which is shown in greater detail in FIG. 3. The sputtering plasma resides at a low plasma potential of between +/−10 volts (+/−10 V). As shown, the repeller 100 comprises a silicon carbide (SiC) threaded block 102, a SiC threaded locking element or sleeve 104, which screws onto the threaded block 102 by means of threads 106, and a sputter electrode slug 108 which is secured to the block 102 by the sleeve 104. The sputter electrode slug 108 may be comprised of aluminum (Al), boron (B), beryllium (Be), carbon (C), cesium (Cs), germanium, (Ge), molybdenum, (Mo), antimony (Sb), silicon (Si), or other suitable material. Generally, a suitable material will have a melting point of greater than 800 degrees Centigrade (800° C.). The threaded block and threaded locking sleeve construction permit sputter electrode slugs 108 of various elements, or compounds thereof, to be easily interchanged.

This electrode material is sputtered away during operation of the source to provide an elemental source of ionizable material that is ionized by the ionized sputtering gas. A positively charged ion beam is extract from the ionization chamber through the source aperture plate 16 by the extraction electrodes 20 and 22 (refer back to FIG. 2). A mass analysis magnet may then be utilized to filter out the positively charged ions in the sputtering gas (e.g., argon) from the positively charged ions generated from the sputter electrode (e.g., boron) to produce the desired ion beam.

Although the use of an inert sputtering gas such as argon has been described, the present invention also contemplates using $BF_3$ as the sputtering gas with a boron repeller, or phosphorous gas as the sputtering gas with a phosphorous repeller. In these latter two cases, ionization of the sputtering gas enhances the ion production caused by the sputtering and subsequent ionization of the repeller material. In the case of $BF_3$ and a boron sputter repeller, 30 milliamps (30 mA) of B+ current has been achieved at ion beam energy levels of only 20 kilo electron volts (20 KeV).

Figure 4:
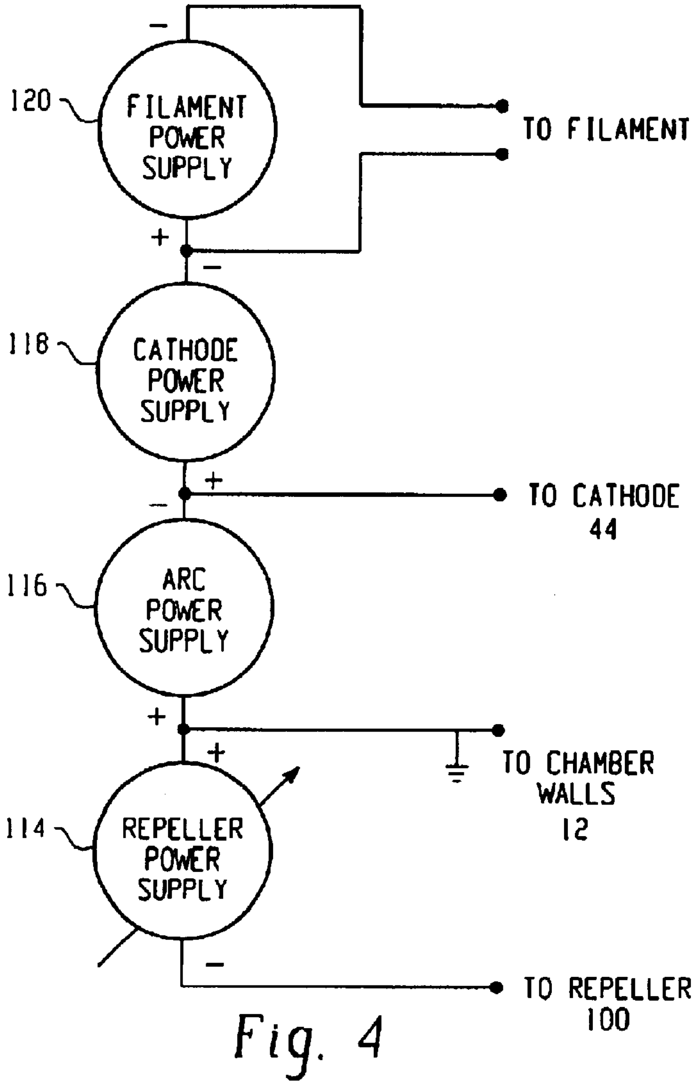
FIG. 4 is an electrical schematic block diagram showing the power supplies that power the ion source of FIG. 2.

The repeller 100 is isolated from the ionization chamber wall 12 by means of an electrical insulator 110. A stem 112 on the threaded block 102 passes through the wall 12 and provides means for connection to a repeller power supply 114 (see FIG. 4). The power supply 114 is used to electrically bias the repeller negatively (with respect to the electrically grounded chamber walls 12). As such, the repeller will effectively function to repel cathodeemitted electrons confined within the ionization chamber 14. Preferably, the power supply 114 is rated at 10 amps (10 A) and is capable of providing up to −2 kilovolts (−2 KV) to the repeller. Typically, the repeller is biased to about −600 volts (−600 V) with respect to the grounded chamber walls.

In addition to the repeller supply 114, an arc power supply 116 is provided to negatively bias the endcap cathode 44 with respect to the grounded chamber walls 12. The negative bias permits the some of the cathode-emitted electrons to accelerate toward the chamber walls to create the arc necessary for ionization of the sputtering gas. The arc power supply 116 is preferably rated at 7 A and is capable of providing up to −150 V. Typically, the arc power supply is operated at about −110 V.

A cathode power supply 118 is provided to positively bias the endcap cathode with respect to the filament. This positive bias permits the filament-emitted electrons to accelerate toward the endcap cathode 44 and cause it to generate cathode-emitted electrons into the ionization chamber. The cathode power supply 118 is preferably rated at 1.6 A and is capable of providing up to −600 V. Typically, the end cap cathode 44 is held at a potential of between 400–500 volts below the local ground of the chamber walls.

Finally, a filament power supply 120 is provided to energize the filament so that it may thermionically generate electrons. The filament power supply 120 is preferably rated at 60 A and is capable of providing up to 10 V. Typically, the filament power supply 120 is operated at between 5–10 volts below the end cap voltage which is sufficient to heat the end cap cathode 44 so that it also thermionically emits electrons into the chamber.

Figure 5:
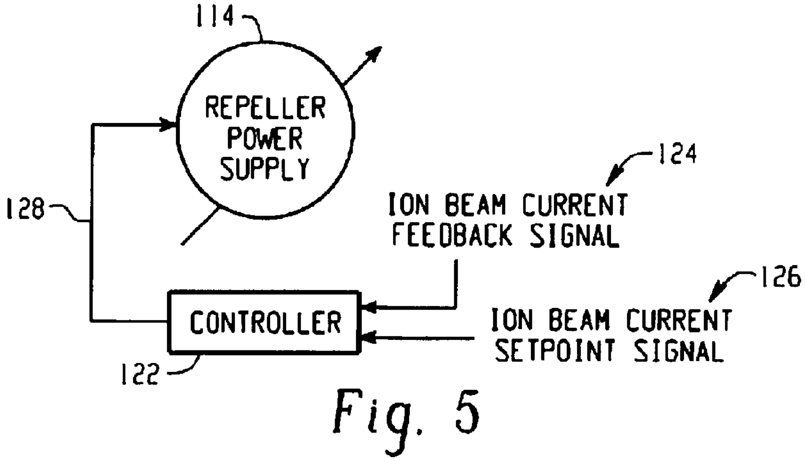
FIG. 5 is an electrical schematic block diagram of the repeller power supply control circuit.

In the preferred embodiment, the repeller power supply 114 is made variable in order to aid in controlling resulting ion beam current. Generally, the higher the repeller voltage (more negative with respect to the chamber walls 12), the higher the energy that is imparted by collisions with the ionized sputtering gas, and the higher the resultant ion beam current withdrawn from the chamber. As shown in FIG. 5, controller 122 uses as its inputs an ion beam current feedback signal 124 and an ion beam current setpoint signal 126. The controller compares signal 122 to signal 124 and outputs a control signal 128 to the repeller power supply 114 based on the difference therebetween. As such, the closed loop control system shown can be used to continuously vary the repeller power supply voltage, based on real-time measurement of ion beam current, to control the ion beam current to desired levels.

In addition, the pressure at which the sputtering gas is provided to the ionization chamber will also effect the degree of sputtering of the sputter electrode 108, and hence, the beam current in the resultant ion beam. In this manner, a combined control system for controlling sputtering gas pressure and for controlling repeller power supply voltage can be employed to provide a wide dynamic range of resulting ion beam currents. The sputtering gas pressure control system could employ a controller similar to controller 122, and also utilize ion beam current feedback signal 124 and ion beam current setpoint signal 126.

Accordingly, a preferred embodiment of a repeller for an ion source has been described. With the foregoing description in mind, however, it is understood that this description is made only by way of example, that the invention is not limited to the particular embodiments described herein, and that various rearrangements, modifications, and substitutions may be implemented with respect to the foregoing description without departing from the scope of the invention as defined by the following claims and their equivalents.

What is claimed is:

1. An ion source for an ion implanter, comprising:

(i) an ionization chamber defined at least partially by chamber walls and having an inlet into which a sputtering gas may be injected, and an aperture through which an ion beam (B) may be extracted;

(ii) an ionizing electron source for ionizing the sputtering gas to form a sputtering plasma; and (iii) a sputterable repeller for (a) repelling electrons emitted by said ionizing electron source, and (b) providing a source of sputtered material that can be ionized by said electron source.

2. The ion source of claim 1, wherein said sputterable repeller comprises a slug of sputterable material, and further comprises mounting structure for mounting said slug within said ionization chamber said slug being removably detachable from said mounting structure.

3. The ion source of claim 2, wherein said sputterable repeller and the electron source are mounted at opposite ends of said ionization chamber.

4. The ion source of claim 2, wherein said mounting structure is comprised of silicon carbide (SiC).

5. The ion source of claim 2, wherein a melting point of said sputterable material is greater than 800 degrees C.

6. The ion source of claim 5, wherein said sputterable material is comprised of any of the following elements, or compounds including any of these elements: aluminum (Al), boron (B), beryllium (Be), carbon (C), cesium (Cs), germanium, (Ge), molybdenum, (Mo), antimony (Sb), or silicon (Si).

7. The ion source of claim 6, wherein the ionizing electron source comprises a heated filament at least partially surrounded by an end cap cathode.

8. The ion source of claim 2, wherein said repeller is electrically isolated from said ionization chamber walls.

9. The ion source of claim 8, wherein said repeller is negatively biased with respect to said ionization chamber walls.

* * * * *